US005763549A

United States Patent [19]

Elder et al.

[11] Patent Number: 5,763,549
[45] Date of Patent: Jun. 9, 1998

[54] CATIONIC METALLOCENE CATALYSTS BASED ON ORGANOALUMINUM ANIONS

[75] Inventors: Michael J. Elder, Raleigh, N.C.; John A. Ewen, Houston, Tex.

[73] Assignee: Fina Technology, Inc., Dallas, Tex.

[21] Appl. No.: 893,522

[22] Filed: Jun. 4, 1992

(Under 37 CFR 1.47)

Related U.S. Application Data

[63] Continuation-in-part of Ser. No. 419,055, Oct. 10, 1989, Pat. No. 5,155,080, and a continuation-in-part of Ser. No. 419,057, Oct. 10, 1989, abandoned.

[51] Int. Cl.⁶ .................................................. C08F 4/642
[52] U.S. Cl. ........................ 526/153; 526/151; 526/160; 502/110; 502/114; 502/117
[58] Field of Search .................................. 502/152, 110, 502/114, 117, 132; 526/151, 153, 160, 154, 155

[56] References Cited

U.S. PATENT DOCUMENTS

| | | | |
|---|---|---|---|
| 4,794,096 | 12/1988 | Ewen | 502/117 |
| 4,892,851 | 1/1990 | Ewen et al. | 502/104 |
| 4,975,403 | 12/1990 | Ewen | 502/113 |
| 5,155,080 | 10/1992 | Elder et al. | 502/152 |
| 5,162,278 | 11/1992 | Razavi | 502/152 |
| 5,198,401 | 3/1993 | Turner et al. | 502/155 |
| 5,272,229 | 12/1993 | Tomotsu et al. | 526/115 |
| 5,369,196 | 11/1994 | Matsumoto et al. | 526/127 |
| 5,407,882 | 4/1995 | Yamada et al. | 502/114 |
| 5,461,128 | 10/1995 | Takeuchi et al. | 526/128 |

FOREIGN PATENT DOCUMENTS

| | | |
|---|---|---|
| 0 277 003 | 8/1988 | European Pat. Off. . |
| 0 277 004 | 8/1988 | European Pat. Off. . |
| 0 423 100A2 | 4/1991 | European Pat. Off. . |

OTHER PUBLICATIONS

Jordan et al., "Ethylene Polymerization by a Cationic Cyclopentadienyl Zirconium(IV) Alkyl Complex", *J. Am. Chem. Soc.*, 1986, 108, pp. 7410–7411.

Cambelli, et al., "Isotactic Polymerization of Propene: Homogeneous Catalysts Based on Group 4 Metallocenes Without Alumoxane", *Macromolecules*, 1989, 22, pp. 2186–2189.

*Primary Examiner*—Romulo H. Delmendo
*Attorney, Agent, or Firm*—Jimmy D. Wheelington; William D. Jackson; M. Norwood Cheairs

[57] ABSTRACT

Metallocene catalysts and their preparation and use in the polymerization of olefins. Specifically, the catalysts and processes relate to polymerization of olefins in which an aluminum ionizing agent containing a triphenylcarbenium ion is utilized in preparing the catalyst. The preparation of an olefin polymerization catalyst comprising a metallocene-type catalyst and triphenylcarbenium tetrakis (pentafluorophenyl)aluminate is disclosed.

28 Claims, No Drawings

CATIONIC METALLOCENE CATALYSTS BASED ON ORGANOALUMINUM ANIONS

This application is a continuation-in-part of U.S. patent application Ser. No. 419,055 filed Oct. 10, 1989, now U.S. Pat. No. 5,155,080 and U.S. patent application Ser. No. 419,057 filed Oct. 10, 1989, now abandoned.

FIELD OF THE INVENTION

This invention relates, in general, to metallocene catalysts and their preparation and use in the polymerization of olefins, and specifically to a catalyst and a process for preparing catalysts for polymerization of olefins in which an aluminum ionizing agent containing a triphenylcarbenium ion is utilized in preparing the catalyst.

More specifically, the invention relates to the preparation of an olefin polymerization catalyst comprising a cationic metallocene and organoaluminum anion.

BACKGROUND OF THE INVENTION

Alpha olefins, especially propylene, may be polymerized to form polyolefins in various forms: isotactic, syndiotactic and atactic. Isotactic polypropylene contains principally repeating units with identical configurations and only a few erratic inversions in the chain. A syndiotactic polymer contains principally repeating units of exactly alternating stereoisomers. A polymer chain showing no regular order of repeating unit configurations is an atactic polymer. In commercial applications, a certain percentage of atactic polymer is typically produced with the isotactic form.

As disclosed in the relevant art, the structure and properties of syndiotactic polypropylene differ significantly from those of isotactic polypropylene. The isotactic structure for polypropylene is typically described as having the methyl groups attached to the tertiary carbon atoms of successive monomeric units on the same side of a hypothetical plane through the main chain of the polymer, e.g., the methyl groups are all above or below the plane. Using the Fischer projection formula, the stereochemical sequence of isotactic polypropylene is described as follows:

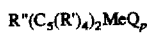

Another way of describing the structure is through the use of NMR. Bovey's NMR nomenclature for an isotactic pentad is . . . mmmm . . . with each "m" representing a "meso" dyad or successive methyl groups on the same side in the plane. As known in the art, any deviation or inversion in the structure of the chain lowers the degree of isotacticity and crystallinity of the polymer.

In contrast to the isotactic structure, syndiotactic polymers are those in which the methyl or other groups attached to the tertiary carbon atoms of successive monomeric units in the chain lie on alternate sides of the plane of the polymer. Syndiotactic polypropylene is shown in zig-zag representation as follows:

Corresponding representations for syndiotactic polyvinylchloride and polystyrene, respectively, are:

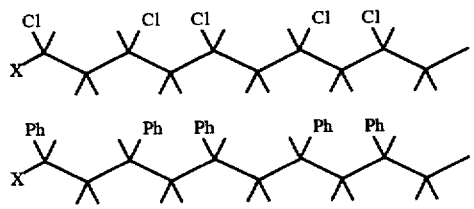

While it is possible for a catalyst to produce all three types of polymers, it is desirable for a catalyst to produce predominantly isotactic or syndiotactic polymer with very little atactic polymer. Catalysts that produce isotactic polyolefins are disclosed in U.S. Pat. Nos. 4,794,096 and 4,975,403. These patents disclose chiral, stereorigid metallocene catalysts that polymerize olefins to form isotactic polymers and are especially useful in the polymerization of a highly isotactic polypropylene.

As described, for example, in the aforementioned U.S. Pat. No. 4,975,403, such chiral stereorigid metallocenes may be characterized by the formula:

$$R''(C_5(R')_4)_2MeQ_p \quad (1)$$

In formula 1, $(C_5(R')_4)$ is a cyclopentadienyl or substituted cyclopentadienyl ring; each R' is the same or different and is a hydrogen or hydrocarbyl radical having 1–20 carbon atoms; R" is a structural bridge between the two $(C_5(R')_4)$ rings imparting stereorigidity to said catalyst, and R"' is selected from the group consisting of an alkylene radical having 1–4 carbon atoms, a silicon hydrocarbyl radical, a germanium hydrocarbyl radical, a phosphorus hydrocarbyl radical, a nitrogen hydrocarbyl radical, a boron hydrocarbyl radical, and an aluminum hydrocarbyl radical: Me is a group 4, 5, or 6 metal as designated in the Periodic Table of Elements; each Q is a hydrocarbyl radical having 1–20 carbon atoms or is a halogen; and $0 \leq p \leq 3$.

Catalysts that produce syndiotactic polypropylene or other syndiotactic polyolefins are disclosed in U.S. Pat. No. 4,892,851. These catalysts are bridged stereorigid metallocene catalysts. The catalysts have a structural bridge extending between dissimilar cyclopentadienyl groups and may be characterized by the formula:

$$R''(CpRn)(CpR'm)MeQ_p \quad (2)$$

In formula (2), Cp represents a cyclopentadienyl ring; and R and R' represent hydrocarbyl radicals having 1–20 carbon atoms. R" is a structural bridge between the rings imparting stereorigidity to the catalyst; R'm is selected so that (CpR'm) is a sterically different substituted cyclopentadienyl ring than (CpRn); n varies from 0 to 4 (0 designating no hydrocarbyl groups, i.e. an unsubstituted cyclopentadienyl ring) and m varies from 1–4, MeQ and p are as described above with reference to formula (1). The sterically different cyclopentadienyl rings produce a predominantly syndiotactic polymer rather than an isotactic polymer. Such bridged structures may be characterized specifically by the foregoing formulas (1) and (2) in which R" denotes a structural bridge between the cyclopentadienyl groups. As noted previously, in formula (2), at least one cyclopentadienyl group is substituted in a manner such that the two groups are sterically different to impart syndiospecificity. Iso-specific structures, as described in the aforementioned patents, U.S. Pat. Nos. 4,794,096 and 4,975,403, can be denoted by a formula similar to formula (2) with the exception that the cyclopentadienyl groups $(C_pR_n)$ and $(C_pR'_m)$ in formula (2) are the same.

European Patent Application 0 277 003 to Turner et al. (Exxon) relates to cationic metallocene catalysts prepared by a proton transfer method. A bis (cyclopentadienyl) metal compound containing at least one substituent capable of reacting with a proton is combined with a second compound having a cation capable of donating a proton and an anion having a plurality of boron atoms. For example, the following reaction illustrates the proton transfer procedure:

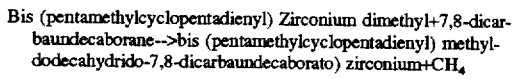

Bis (pentamethylcyclopentadienyl) Zirconium dimethyl+7,8-dicarbaundecaborane-->bis (pentamethylcyclopentadienyl) methyldodecahydrido-7,8-dicarbaundecaborato) zirconium+CH$_4$ European Patent Application 0 277 004 to Turner (Exxon Chemicals) also relates to catalysts prepared by a proton transfer method. A bis(cyclopentadienyl) metal compound is combined with a second ionic compound having a cation that will irreversibly react with a ligand on the metal compound and an anion having a plurality of lipophilic radicals around a metal or metalloid ion. The following reaction illustrates this procedure:

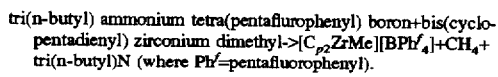

tri(n-butyl) ammonium tetra(pentaflurophenyl) boron+bis(cyclopentadienyl) zirconium dimethyl->[C$_{p2}$ZrMe][BPh$^f_4$]+CH$_4$+ tri(n-butyl)N (where Ph$^f$=pentafluorophenyl).

A by-product of the proton transfer reaction is a Lewis base (amine), some of which can coordinate to the cations and thus inhibit catalyst activity. In the proton transfer reaction, starting materials must be chosen carefully to avoid generating particular amines that can poison catalysts. In addition, the catalyst and the polymer produced with this catalyst contains undesirable and toxic residual amines.

In most known metallocene catalyst processes, methylalumoxane (MAO) is added with the metallocene to act as a cocatalyst. MAO functions as an alkylating agent which according to one theory of operation also promotes ionization of the metallocene catalyst. The cocatalyst can serve as a scavenging agent that reduces basic impurities from the reaction medium which may decrease catalyst activity. MAO is quite expensive, and its high cost results in increased costs for any catalyst system utilizing MAO.

Bis(cyclopentadienyl) complexes in the presence of MAO polymerize ethylene with high efficiency. The metal in such complexes is typically titanium, zirconium, or hafnium, but may be any metal from Group 4, 5, or 6 (new notation) of the Periodic Table of Elements. It has been postulated that the active catalyst for this type of soluble Ziegler-Natta catalyst involves cationic d° alkyl complexes associated with a labile stabilizing anion (see Jordan et al., J. Am. Chem. Soc. 1986, 108, 7410–7411 and references therein). When employing a stereorigid bridged metallocene in conjunction with MAO the resulting catalyst system can be used to polymerize propylene to highly isotactic, hemiisotactic, or syndiotactic forms of propylene.

As is well known, the soluble metallocene catalyst systems offer several advantages over conventional heterogeneous Ziegler-Natta catalysts including higher catalyst activities, the production of polymers with narrow molecular weight distributions, and the synthesis of highly syndiotactic polymers which are not possible with conventional catalysts. It is also well known that high concentrations of MAO are required by metallocene catalyst systems which are costly and results in a high polymer ash content requiring additional post-reactor treatment before the polymer can be used.

Group 4 metallocenes in the presence of only trialkylaluminum compounds such as $R_nAlX_{3-n}$ (where R=alkyl X=halide and n is from 1–3) are not known to polymerize alpha olefins appreciably with the exception of mixtures of trimethylaluminum and dimethyl-aluminum fluoride recently reported by Zambelli, Longo, and Grassi, "Isotactic Polymerization of Propene: Homogenous Catalysts Based on Group 4 Metallocenes Without Methylalumoxane" Macromolecules 1989, 22, 2186–2189. The present invention need not, however, utilize a neutral Lewis acid such as dimethylaluminum fluoride, and the Zambelli et al. disclosure does not contemplate forming discrete cyclopentadienyl-containing metallocene cations. Furthermore, Zambelli et al. do not contemplate triphenylcarbenium aluminum ionizing agents as used in conjunction with the present invention.

The previously mentioned Exxon patent application publication 0 277 004 describes a method for preparing base free $(C_{p2}Zr(CH_3))[BPh_4]$ type ethylene polymerization catalysts by protonation of a $C_{p2}Zr(CH_3)_2$ methyl group with [R$_3$NH] [BPh$_4$] in hydrocarbon solvent. The Exxon application describes the use of [BPh$^f_4$] as a counterion with a stereorigid bridged cationic metallocene for the production of isotactic polypropylene. [BPh$^f_4$] is equivalent to B(C$_6$F$_5$)$_4$ wherein the phenyl groups are fully and completely fluorinated. The Exxon application does not disclose aluminum ionizing agents, however, and there is no teaching or indication of any triphenylcarbenium aluminum ionizing agents in the Exxon '004 patent application.

SUMMARY OF THE INVENTION

In accordance with the present invention there is provided a cationic metallocene cayalyst characterized in accordance with formula (4) below and a process for the preparation of a cationic metallocene catalyst. Furthermore, this invention relates to a process for the polymerization of alpha olefins by providing a cationic metallocene catalyst prepared by the reaction of a neutral metallocene ligand containing at least one substituent capable of reactions with a carbenium ion and a triphenylcarbenium aluminim ionizing agent.

In carrying out the invention there is provided a neutral metallocene characterized by the formula:

(Cp') (Cp") MQ$_k$ (3)

Each of Cp' and Cp" is a cyclopentadienyl or a hydrocarbyl substituted cyclopentadienyl group. Cp' and Cp" are the same (as in formula 1 above) or different (as in formula 2 above) and they may be bridged as in both formulas (1) and (2) or they may be unbridged. M is Group 4, 5 or 6 metal and Q is a hydride, a halogen, or a hydrocarbyl radical. Each Q is the same or different, except only one Q is a hydride and k is from 2 to 3.

Unbridged metallocenes in which the cyclopentadienyl rings are free to rotate about their coordination axes can, as indicated previously, be used in the polymerization of ethylene. Stereorigid metallocene structures such as the bridged isospecific or syndiospecific structures depicted specifically by formulas (1) and (2) above may, of course, be used in the polymerization of C$_{3+}$ alpha olefins, particularly propylene. In each of these cases, the neutral metallocene structure may be reacted with a triphenylcarbenium aluminum ionizing agent as indicated below to produce a cationic metallocene catalyst depicted by the formula:

[(Cp')(Cp")MQ$_k$]$^+$ [AlR'''$_4$]$^-$ (4)

Here, Cp', Cp", M and Q are as described previously, L is 1 or 2, and R'" is an aklyl, a hydride, a halogen, an alkoxy, aryloxy, an aryl group or substituted aryl group, each R'" being the same or different, except only one R'" is a hydride.

The neutral metallocene may be substituted with several different groups, including but not limited to hydrocarbons such as methyl groups and/or other ring structures. The resulting cationic metallocene catalysts may comprise Cp groups that are the same or different. If the Cp groups are the same, the resulting cationic metallocene catalysts can be used to produce isotactic polymer product. If the Cp groups are different, the resulting cationic metallocene catalysts can be used to produce syndiotactic polymer product. The specific groups substituted on the cyclopentadienyl rings thus can be determinative of whether the resulting cationic metallocene catalyst produces isotactic, syndiotactic or atactic polymer product.

The cyclopentadienyl groups may be and probably are bridged to provide isospecific or syndiospecific catalysts. Thus, it will be understood that the formula, (Cp') (Cp") $MQ_k$ is inclusive of metallocene ligand structures which are substituted in a manner to provide a structural bridge between the cyclopentadienyl groups prior to reaction with the triphenylcarbenium ionizing agent to form the ionic complex.

The present invention involves the use of a discrete aluminum ionizing agent useful as a polymerization catalyst when combined with metallocenes. In a preferred embodiment of the invention the triphenylcarbenium aluminum ionizing agent is triphenylcarbenium tetrakis (pentafluorophenyl)aluminate. Furthermore, in the preparation of a cationic metallocene catalyst in accordance with an embodiment of the invention there is employed a neutral metallocene precursor comprising a stereorigid metallocene characterized by a metallocene ligand having two sterically similar or dissimilar ring structures joined to a coordinating transition metal atom. The ring structures may or may not comprise substituted or unsubstituted cyclopentadienyl groups in a stereorigid relationship relative to the metal atom. In further embodiments of the present invention, a structural bridge may extend between similar or dissimilar ring structures as described above.

The neutral metallocene may comprise a first cyclopentadienyl ring structure that is substituted or unsubstituted and a second cyclopentadienyl ring structure which is substituted and sterically different from the first ring structure.

The present invention makes MAO unnecessary in some cases, but there may be MAO present in the reaction. The present invention further involves the use of a trialkylaluminum compound in conjunction with an aluminum ionizing agent to alkylate and ionize the neutral metallocene and react with basic impurities present in the reaction medium.

In carrying out the invention, a neutral metallocene is provided in reaction with a triphenylcarbenium aluminum ionizing agent and trialkylaluminum. The neutral metallocene and the triphenylcarbenium aluminum ionizing agent are contacted under conditions that cause ionization of the metallocene by the triphenylcarbenium aluminum ionizing agent thereby forming an ion pair in which the metallocene has catalytic activity for the polymerization of olefins. More specifically, a trialkylaluminum is employed under conditions that cause alkylation of the metallocene in conjunction with ionization by the triphenylcarbenium ionizing agent. The neutral metallocene in the process is characterized by the presence of at least two cyclopentadienyl or substituted cyclopentadienyl groups which may be connected through a bridging group, and coordinated with a metal atom from Group 4, 5, or 6 (new notation) of the Periodic Table of Elements, and having at least two other groups (referred to here as Q groups) coordinated to the metal, which groups may be a hydride, a halogen, an amide, or a hydrocarbyl radical. The preferred metal is a Group 4 metal, and most preferably zirconium, although titanium, hafnium and Group 5, and 6 metals may also be used. A preferred embodiment of the present invention uses a group comprising chlorine, although other groups may be used as well.

The ionized metallocene is characterized by an aluminum anion group $AlR'''_4$, which is not coordinated or is only loosely coordinated with the metallocene cation, and is chemically unreactive with the cation. The metallocene cation contains at least one Q group as described above and preferably a hydride or a hydrocarbyl radical. In the preferred embodiment of the invention it is contemplated that the catalyst will be used to polymerize propylene, although ethylene, styrene, and other monomers may be polymerized with the present invention.

DETAILED DESCRIPTION OF THE INVENTION

The present invention is particularly applicable to bridged stereo-rigid metallocene ligands which are especially suitable in the polymerization of alpha olefins to produce stereo-specific polymers, for example, isotactic and syndiotactic polypropylene. It is also applicable to metallocene ligands in which the cyclopentadienyl groups are not bridged. Both bridged and unbridged metallocenes are known in the art to be useful in the polymerization and copolymerization of ethylene to produce polyethylene and co-polymers such as ethylene-propylene co-polymers. With respect to bridged stereo-rigid metallocene ligands, they may be the same or different to produce isotactic or syndiotactic polymers. By way of example, chiral ethylene bridged bis (indenyl) metallocene structures are useful in the catalysis of polymerization reactions leading to isotactic polypropylene whereas bridged ligand structures such as isopropyl (cyclopentadienyl) (fluorenyl) metallocene ligand structures are useful as catalysts in the production of syndiotactic polypropylene. For a description of other metallocene structures to which the present invention may be applied, reference is made to European Patent Application Publication No. 0423100A2 published Apr. 17, 1991, the entire disclosure of which is incorporated by reference.

Catalysts employing stereorigid cationic metallocene catalyst systems without MAO polymerize propylene with high efficiency yielding polymers with low ash content. However, catalyst stereospecificity is reduced relative to the MAO based catalyst when certain metallocenes are paired with —$BPh^f_4$, resulting in polymers of lower crystallinity. Such polymers are less desirable. This is especially true for the syndiospecific metallocene $iPr[C_p(Flu)]ZrCl_2$ (where iPr=isopropylidene interannular bridge and Flu=fluorenyl group).

The present invention provides an alternative anion for use in metallocene reactions that will not adversely affect the stereochemistry of the catalyst. The aluminum ionizing agent of the present invention provides a new aluminum-based metallocene catalyst and process.

The present invention relates to a discrete aluminum ionic compound useful as a polymerization catalyst when combined with metallocenes, a method of preparing catalysts, and a process for using the catalysts for the polymerization of olefins. A preferred specific application of the invention relates to the use of triphenylcarbenium tetrakis (pentafluorophenyl)aluminate [Ph₃C][AlPh'₄] as an ionizing agent. When combined with certain stereorigid metallocenes, for example, syndiospecific iPr[C_p(Flu)]ZrCl₂, the resulting metallocene cation -aluminum anion pair provides higher crystallinity polymers than those obtained with cationic metallocenes derived from boron-containing anions such as —BPh'₄. Furthermore, the catalysts have the advantage of requiring a lower total Al/Zr mole ratio than the MAO based catalysts.

In "Polyfluoroaryl Organometallic Compounds, Part IV. Fluorocarbon Derivatives of Tricovalent Aluminum", *J. Chem. Soc.* (C), 1967, p. 2185 by Chambers and Cunningham, it was reported that the formation of a white solid residue resulting from an anionic aluminum compound was synthesized by the reaction of pentafluorophenyl-lithium with aluminum tribromide in hydrocarbon solvents. Chambers and Cunningham reported the formation of white solid residue containing pentafluorophenyl but could not extract any single lithium-aluminum species with a variety of solvents.

The present invention goes far beyond the activity described in the Chambers article in that the inventors in the present case have isolated a triphenylcarbenium aluminum compound, and have shown that such a compound is useful in the polymerization of alpha olefins.

In carrying out the invention there is provided a neutral metallocene characterized as described previously by the formula:

(Cp') (Cp") MQ_k     (3)

wherein Cp', Cp", MQ, and k are as described above. More specific and preferred neutral metallocenes are bridged metallocenes as characterized by formulas (1) and (2) above. In addition there is provided a triphenylcarbenium aluminum ionizing agent which does not contain an active proton. The ionizing agent is characterized by the formula:

[Ph₃C] [AlR'''₄]     (5)

In formula (5) Ph is a phenyl group or a substituted phenyl group. R''' may be a hydride, a halogen, or a hydrocarbyl radical, more specifically an alkyl or aryl group or an akloxy, aryloxy, or substituted aryl group, each R' being the same or different, except only one R''' is a hydride.

The neutral metallocene and aluminum ionizing agent are contacted under conditions to cause ionization of the neutral metallocene by the ionizing agent to form an ion pair comprising a metallocene cation having catalytic activity in olefin polymerization and an AlR'''₄ anion, the latter being not coordinated or only loosely coordinated to the metallocene cation and, chemically unreactive with the metallocene cation. Where R''' is a halogen the metallocene is alkylated with a trialkylaluminum such as TEAL.

In a preferred embodiment of the present invention, a cyclopentadienyl metal compound, in which the metal is selected from Group 4, 5 or 6 of the Periodic Table of Elements, said compound containing a Q group which is a hydride, halogen, amide, or hydrocarbyl radical, is combined with a triphenylcarbenium aluminum ionizing agent and trialkylaluminum alkylating agent. The triphenylcarbenium aluminum ionizing agent does not contain an active proton and when combined, the neutral metallocene compound is ionized by the triphenylcarbenium aluminum ionizing agent to form an ion-pair in which the metallocene cation has catalytic activity for the polymerization of an olefin.

Furthermore, the AlR'''₄ anion, which is not coordinated or is only loosely coordinated to the metallocene cation, is chemically unreactive with the metallocene cation. The transition metal of the metallocene is preferably selected from the group consisting of zirconium, hafnium and titanium with zirconium being most preferred followed by hafnium and titanium, respectively. However, as noted previously, it is contemplated that other metals of Groups 5 and 6 of the periodic table may serve in the present invention.

In a particularly preferred embodiment of the present invention, iPr[C_p(Flu)]ZrCl₂ is utilized in the preparation of the catalyst and is contacted with triethylaluminum and [Ph₃C] [AlPh'4] in toluene solution. These components will be combined at a temperature within the range from about 0° C. to about 50° C. The components will be combined, preferably, in an aromatic hydrocarbon solvent, most preferably toluene. Nominal holding times within the range of from about ten seconds to about sixty minutes will be sufficient to produce the preferred catalyst of this invention.

In a further aspect of the invention, the catalyst, immediately after formation, is used to polymerize an olefin, particularly ethylene or propylene and most preferably propylene, at a temperature within the range from about 0° C. to about 100° C. and at a pressure within the range from about 25 to about 600 psig. It will be understood that other monomers besides propylene and ethylene may be polymerized using the catalyst of the present invention, and this disclosure should not be construed as limiting polymerization to any particular polymer or monomer.

Having thus broadly described the present invention and the preferred embodiments thereof, reference is made to the following experimental work to further characterize the invention. It will be appreciated that the experimental work should not be construed as limiting the invention. The aluminum and metallocene reagents used in the examples were either purchased or prepared following published techniques or procedures described below.

Experimental work respecting the present invention was carried out employing syndiospecific and isospecific metallocenes with two different triphenylcarbenium ionizing agents, (Ph₃C)(AlPh'₄) and (Ph₃C)(BPh'₄), and with methylalumoxane. The results of this experimental work are set forth in Tables I and II below. The following Example illustrates the preparation of a preferred triphenylcarbenium ionizing agent, (Ph₃C)(AlPh'₄) used in the experimental work.

EXAMPLE 1

16 mmol of bromopentafluorobenzene were diluted with 60 mL of toluene, cooled to −78° C., and one equivalent of butyllithium (1.6M solution in hexane) was added slowly. Pentafluorophenyllithium precipitated as a white solid during the reaction. After stirring for 2 hrs. at −78° C., 4 mmol of AlBr₃ dissolved in 15 mL of toluene were added slowly. The reaction mixture was cautiously warmed to room temperature and 4 mmol of triphenylmethyl chloride dissolved in 20 mL of methylene chloride were added resulting in an orange slurry. After filtration, solvents were removed from the filtrate in vacuo and the orange residue was thoroughly triturated with pentane. The resultant moderately air sensitive yellow solids were collected on a closed filter and washed for 12 hrs. with boiling hexane in an extraction assembly. The yield was 2.45 g of bright yellow powder (65%). The calculated wt parts for C₄₃H₁₅F₂₀Al are: C, 54.81; H, 1.62. The amounts found by elemental analysis are: C, 51.97; H, 1.62 The molecular structure is characterized by the following NMR data presented in standard notation: H-NMR (CD$_2$Cl$_2$); chemical shifts in ppm: 8.26 (t, 1H), 7.87 (t, 2H), 7.66 (d, 2H). F-NMR (CD$_2$Cl$_2$), relative to C$_6$F$_6$ @ -163.7 ppm int. ref.:-123.6 (2 F), -159.4 (1 F), -165.5 (2 F).

The following Examples 2 and 3 are illustrative of polymerization procedures carried out with the preferred triphenylcarbenium tetrakis(pentafluorophenyl)aluminate ionizing agent, (Ph$_3$C)(AlPhf$_4$), and alumoxane, both used in conjunction with a syndiospecific metallocene.

EXAMPLE 2

5.2 mL of a 0.15M triethylaluminum (TEAl) solution in hexane were added to 1.3 mg of iPr[C$_p$(Flu)ZrCl$_2$ slurried in 10 mL of toluene giving a bright yellow solution. The metallocene solution was added to a dry two liter jacketed autoclave equipped with a magnedrive stirrer followed by 1,000 mL of propylene. The polymerization was initiated by adding 5.6 mg of [Ph$_3$C][AlPh$^f_4$] as a toluene solution (10 mL) with 400 mL of propylene at room temperature. The catalyst was prepolymerized on heating the reactor, with stirring, to the reaction temperature (60° C.) within five minutes of [Ph$_3$C][AlPh$^f_4$] addition. The polymerization was terminated by venting all unreacted monomer. If the yield was less than 50 g, toluene was added to the reaction products and the polymer/toluene slurry was washed with a 50/50 methanol/4N HCl solution and then water. The aqueous layer was separated and toluene was removed from the polymer with a rotoevaporator.

EXAMPLE 3

0.5 mg of iPr[Cp(Flu)]ZrCl$_2$ were dissolved in 5.0 mL of a 10 wt % methylalumoxane (MAO) solution in toluene and added to a 40 mL stainless steel bomb equipped with ball valves on each end. The average molecular weight of the MAO was about 1,100 grams per mole. The catalyst solution was charged to a 2 liter autoclave reactor which contained 1 liter of propylene at room temperature. The catalyst was prepolymerized on heating the reactor contents, with stirring, to reaction temperature (60° C.) within five minutes after charging. The polymerization was terminated by venting all unreacted monomer. If the yield was less than 50 g, toluene was added to the reaction products and the polymer/toluene slurry was washed with a 50/50 methanol/4N HCl solution and then water. The aqueous layer was separated and toluene was removed from the polymer with a rotoevaporator.

The results of experimental work carried out employing the syndiospecific metallocene, isopropylidene (cyclopentadienyl) (9-fluorenyl)zirconium dichloride, are set forth in Table I. The results of the experimental work carried out employing the isospecific metallocene, ethylene bis(indenyl) zirconium dichloride, are presented in Table II. In each of Tables I and II, the quantities of metallocene, of the appropriate catalyst component A as designated in the Table, and of TEAL are shown in the first, second and third columns, respectively. The reaction temperature and time are shown in the fourth and fifth columns, respectively, and the polymer yield in the sixth column. The intrinsic viscosity and melting point are shown in the seventh and eighth columns, respectively and the percent of racemic (Table I) or meso (Table II) pentads for the polymer products is shown in the last column of each Table.

TABLE I

SYNDIOSPECIFIC iPr[Cp(Flu)]ZrCl$_2$
PROPYLENE POLYMERIZATION RESULTS[a]

| Zirconocene, mg | A, mg | TEAL, mmol | T, °C. | t, min. | Yield, g | [n],[b] dl/g | m. pt.,[c] °C. | rrr, % |
|---|---|---|---|---|---|---|---|---|
| A = [Ph$_3$C][AlPh$_4^f$] | | | | | | | | |
| 5.0 | 40.0 | 2.00 | 50 | 60 | 100 | 1.24 | 138 | 83.7 |
| 1.0 | 9.0 | 2.00 | 50 | 30 | 15 | 1.05 | 138 | |
| 1.3 | 6.0 | 0.78 | 60 | 60 | 14 | | 142 | |
| 1.3 | 11.2 | 0.78 | 60 | 70 | 48 | 1.17 | 139 | |
| 1.3 | 16.8 | 0.78 | 60 | 60 | 22 | | 141 | |
| A = [Ph$_3$C][BPh$_4^f$] | | | | | | | | |
| 0.5 | 6.0 | 0.66 | 50 | 60 | 56 | 1.12 | 129 | 80.0 |
| 0.5 | 6.0 | 2.00 | 50 | 60 | 47 | 1.13 | 131 | 79.0 |
| A = MAO | | | | | | | | |
| 0.5 | 450 | 0.00 | 50 | 60 | 39 | | 140 | 85.8 |
| 0.5 | 450 | 0.00 | 60 | 60 | 138 | 1.29 | 136 | |

[a] 1400 mL of liquid propylene.
[b] Intrinsic viscosity; determined from 135° C. decahydronapthalene solutions.
[c] DSC melting points of samples previously heated to 450K, held at this temperature for 5 minutes, and cooled at 10K/min with baseline correction.
[d] $^{13}$C-NMR results for 20% (w/w) polymer solutions in 1,2,4-trichlorobenzene/d$_6$-Benzene.

TABLE II

ISOSPECIFIC Et[Ind]₂ZrCl₂ PROPYLENE POLYMERIZATION RESULTS[a]

| Zirconocene, mg | A, mg | TEAL, mmol | T, °C. | t, min. | Yield, g | [n],[b] dl/g | m. pt.,[c] °C. | mmmm,[d] % |
|---|---|---|---|---|---|---|---|---|
| A = [Ph₃C][AlPh₄[f]] | | | | | | | | |
| 5.0 | 40.0 | 2.00 | 50 | 60 | 56 | 0.57 | 140 | 86.5 |
| 1.3 | 11.2 | 0.78 | 60 | 60 | 24 | 0.63 | 141 | 85.8 |
| A = [Ph₃C][BPh₄[f]] | | | | | | | | |
| 0.6 | 5.6 | 0.78 | 60 | 30 | 27 | 0.49 | 135 | 85.5 |
| A = MAO | | | | | | | | |
| 1.0 | 450 | 0.00 | 60 | 30 | 97 | 0.51 | 135 | 85.5 |

[a] 1400 mL of liquid propylene.
[b] Intrinsic viscosity; determined from 135° C. decahydronapthalene solutions.
[c] DSC melting points of samples previously heated to 450K, held at this temperature for 5 minutes, and cooled at 10K/min with baseline correction.
[d] ¹³C-NMR results for 20% (w/w) polymer solutions in 1,2,4-trichlorobenzene/d₆-Benzene.

From an examination of the data in the foregoing Tables I and II, it can be seen that catalyst activity with the aluminum ionizing agent is lower than the activity relating to the use of MAO or boron ionizing agents. Also, it will be recognized that the identity of the catalyst component, whether it be aluminum, boron, or MAO has little effect on intrinsic viscosity. The intrinsic viscosity is noted by the quantity [n] as set forth in Table I and Table II. In general, it is desirable for the intrinsic viscosity of the polymer product to be about one dl/g or higher.

The experimental work reported in Table I and Table II indicates that aluminum containing ionizing agents produce polymers that are more crystalline, and more stereoregular than boron. The crystallinity of the polymer is indicated by the melting point figures in Table I and Table II. It can be seen that, in general, the runs with an aluminum based catalyst component in Table II show a higher melting point, and a correspondingly higher crystallinity, than catalyst components produced with the boron ionizing agent or with MAO. With regard to the syndiospecific results in Table I, the same general relationship is observed.

Having described specific embodiments of the present invention, it will be understood that modifications thereof may be suggested to those skilled in the art, and it is intended to cover all such modifications as fall within the scope of the appended claims.

We claim:

1. In a process for the preparation of a cationic metallocene catalyst, the steps comprising
   a) providing a neutral metallocene olefin polymerization catalyst precursor containing at least one substituent capable of reacting with a carbenium ion;
   b) providing a triphenylcarbenium aluminum ionizing agent which does not contain an active proton and is characterized by the formula (Ph₃C)(AlR'''₄), wherein Ph is a phenyl group or a substituted phenyl group, R''' is an alkyl, a hydride, a halogen, an alkoxy, an aryloxy, an aryl group or a substituted aryl group, each R''' being the same or different, provided that no more than one R''' is a hydride;
   c) providing a trialkyl aluminum; and
   d) contacting together said neutral metallocene, said trialkyl aluminum and said triphenylcarbenium aluminum ionizing agent under conditions to cause alkylation and ionization of said neutral metallocene by said triphenylcarbenium aluminum ionizing agent to form an ion pair comprising a metallocene cation having catalytic activity in olefin polymerization and an AlR'''₄ anion, which is chemically unreactive with the metallocene cation.

2. The process of claim 1, wherein said neutral metallocene is in the form of a stereorigid metallocene characterized by a metallocene ligand having two sterically identical or non-identical ring structures joined to a coordinating transition metal atom, each of said ring structures being a hydrocarbyl substituted or unsubstituted cyclopentadienyl group and in a stereorigid relationship relative to said coordinating transition metal atom to prevent rotation of said ring structure about said metal atom.

3. The process of claim 2, wherein said neutral metallocene is characterized by a structural bridge extending between said identical or non-identical ring structures.

4. The process of claim 3, wherein said neutral metallocene comprises a first cyclopentadienyl ring structure which is substituted with a hydrocarbyl group or unsubstituted and a second cyclopentadienyl ring structure which is substituted with a hydrocarbyl group and which is sterically different from said first cyclopentadienyl ring structure.

5. The method of claim 4, wherein the transition metal of said neutral metallocene is a Group IV or Group V metal from the Periodic Table of Elements.

6. The method of claim 5, wherein said transition metal is titanium, zirconium or hafnium.

7. In a process for making a cationic metallocene catalyst, the steps comprising
   a) providing a neutral metallocene characterized by the formula:

(Cp')(Cp'')MQ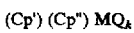

wherein:
   Cp' and Cp'' are each a cyclopentadienyl or a hydrocarbyl substituted cyclopentadienyl group and are the same or different,
   M is a Group 4, 5, or 6 metal,
   Q is a hydride, a halogen, or a hydrocarbyl radical, each Q being the same or different, except only one Q can be a hydride and k is from 2 to 3;
   b) providing a triphenylcarbenium aluminum ionizing agent which does not contain an active proton and is characterized by the formula:

$$[Ph_3C][AlR'''_4]$$

wherein: Ph is a phenyl group or a substituted phenyl group, R''' is an alkyl, a hydride, a halogen, an alkoxy, an aryloxy, a hydrocarbyl radical, an aryl group or substituted aryl group, each R''' being the same or different, except only one R''' is a hydride;

c) providing a trialkyl aluminum; and d) contacting together said neutral metallocene, said trialkyl aluminum and said triphenylcarbenium aluminum ionizing agent under conditions to cause alkylation and ionization of said neutral metallocene by said triphenylcarbenium aluminum ionizing agent to form an ion pair comprising a metallocene cation having catalytic activity in olefin polymerization and an AlR'''$_4$ anion, which is chemically unreactive with the metallocene cation.

8. A process as recited in claim 7, wherein M is a Group IV metal chosen from the group consisting of titanium, zirconium and hafnium.

9. A process as recited in claim 8, wherein M is hafnium.

10. A process as recited in claim 8, wherein M is zirconium.

11. A process as recited in claim 10, wherein each Q is a a hydride or hydrocarbyl radical.

12. A process as recited in claim 11, wherein each R''' is a pentafluorophenyl group.

13. The method of claim 7, wherein the ion pair produced in step (c) is characterized by the formula:

$$[(Cp')(Cp'') MQ_L]^+ [AlR'''_4]^-$$

wherein:

Cp', Cp'', Q, and R''' are as defined in claim 8;

L is 1 or 2;

and the AlR'''$_4^-$ anion is chemically unreactive with the metallocene cation.

14. A process for the polymerization of alpha olefins comprising a. providing a cationic metallocene catalyst prepared by the process of contacting together a neutral metallocene olefin polymerization catalyst precursor containing at least one substituent capable of reacting with a carbenium ion, a triphenylcarbenium aluminum ionizing agent which does not contain an active proton and is characterized by the formula (Ph$_3$C)(AlR'''$_4$), wherein Ph is a phenyl group or a substituted phenyl group, R''' is an alkyl a hydride, a halogen, an alkoxy, an aryloxy, an aryl group or a substituted aryl group, each R''' being the same or different, provided that no more than one R''' is a hydride; and a trialkyl aluminum under conditions to cause alkylation and ionization of said neutral metallocene by said triphenylcarbenium aluminum ionizing agent to form an ion pair comprising a metallocene cation having catalytic activity for olefin polymerization and an AlR'''$_4$ anion which is not coordinated to the metallocene cation and is chemically unreactive with the metallocene cation; and b. contacting said catalyst in a polymerization reaction with an alpha olefin under polymerization conditions to produce polymerization of said alpha olefin.

15. The process of claim 14 wherein said metallocene is a stereorigid metallocene characterized by a metallocene ligand having two sterically similar or dissimilar ring structures which are sterically the same or different joined to a coordinating transition metal atom, each of said ring structures being a hydrocarbyl substituted or unsubstituted cyclopentadienyl group and in a stereorigid relationship relative to said coordinating transition metal atom to prevent rotation of said ring structure about said metal atom.

16. The process of claim 15 wherein said metallocene is characterized by a structural bridge extending between said same or different ring structure.

17. The process of claim 16 wherein said a metallocene of a Group IV metal selected from the group consisting of titanium, zirconium, and hafnium.

18. The process of claim 17 wherein said alpha olefin is propylene.

19. The process of claim 18 wherein said Group IV metal is zirconium.

20. A metallocene catalyst comprising a cationic metallocene characterized by the formula:

$$[(Cp')(Cp'') MQ_L]^+ [AlR'''_4]^-$$

wherein

Cp' and Cp'' are each a cyclopentadienyl or a hydrocarbyl substituted cyclopentadienyl group and are the same or different, M is a Group 4, 5, or 6 metal, Q is a hydride, or a hydrocarbyl radical, each Q being the same or different, except only one Q is a hydride, L is 1 or 2, R''' is an alkyl, a hydride, a halogen, an alkoxy, aryloxy, a hydrocarbyl radical, an aryl group or substituted aryl group, each R''' being the same or different, except only one R''' is a hydride, prepared by the process of contacting together a neutral metallocene characterized by the formula:

$$(Cp') (Cp'') MQ_k$$

wherein Cp' and Cp'', M and Q are each as defined above and k is from 2 to 3, a triphenylcarbenium aluminum ionizing agent which does not contain an active proton and is characterized by the formula:

$$[Ph_3C] [AlR'''_4]$$

wherein Ph is a phenyl group or a substituted phenyl group and R''' is as defined above, and a trialkyl aluminum, under conditions to cause alkylation and ionization of said neutral metallocene by said triphenylcarbenium aluminum ionizing agent.

21. A catalyst as recited in claim 20 wherein M is a Group IV metal chosen from the group consisting of titanium zirconium, and hafnium.

22. A catalyst as recited in claim 21 wherein R''' is a phenyl or substituted phenyl group.

23. A catalyst as recited in claim 22 wherein R''' is pentafluorophenyl group.

24. A catalyst as recited in claim 20 wherein M is zirconium.

25. A catalyst as recited in claim 20 wherein Q is a alkyl group.

26. A catalyst as recited in claim 25 wherein R''' is a pentafluorophenyl group.

27. A catalyst as recited in claim 26 wherein L is 1.

28. In a process for the polymerization of alpha olefins comprising contacting the metallocene catalyst of claim 27 with an alpha olefin under polymerization conditions.

* * * * *